United States Patent
Hasegawa et al.

(10) Patent No.: US 12,415,157 B2
(45) Date of Patent: Sep. 16, 2025

(54) METHOD FOR PRODUCING PURIFIED GAS, METHOD FOR PRODUCING VALUABLE MATERIAL, GAS PURIFICATION DEVICE, AND DEVICE FOR PRODUCING VALUABLE MATERIAL

(71) Applicant: SEKISUI CHEMICAL CO., LTD., Osaka (JP)

(72) Inventors: Tomoya Hasegawa, Tokyo (JP); Kazuto Natsuyama, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 650 days.

(21) Appl. No.: 17/761,409

(22) PCT Filed: Sep. 23, 2020

(86) PCT No.: PCT/JP2020/035837
§ 371 (c)(1),
(2) Date: Mar. 17, 2022

(87) PCT Pub. No.: WO2021/060289
PCT Pub. Date: Apr. 1, 2021

(65) Prior Publication Data
US 2022/0347624 A1 Nov. 3, 2022

(30) Foreign Application Priority Data
Sep. 24, 2019 (JP) .................................. 2019-172541

(51) Int. Cl.
*B01D 53/047* (2006.01)
*B01D 53/00* (2006.01)
*C07C 29/151* (2006.01)

(52) U.S. Cl.
CPC ....... *B01D 53/0476* (2013.01); *B01D 53/002* (2013.01); *C07C 29/1518* (2013.01); *B01D 2253/102* (2013.01); *B01D 2253/108* (2013.01)

(58) Field of Classification Search
CPC .............. B01D 53/0476; B01D 53/002; B01D 2253/102; B01D 53/047; C10K 1/024;
(Continued)

(56) References Cited

U.S. PATENT DOCUMENTS

| | | |
|---|---|---|
| 2018/0318750 A1 | 11/2018 | Zhong et al. |
| 2019/0256874 A1 | 8/2019 | Fujimori et al. |

FOREIGN PATENT DOCUMENTS

| | | |
|---|---|---|
| CN | 105749699 | 7/2016 |
| CN | 107096370 | 8/2017 |

(Continued)

OTHER PUBLICATIONS

JP 2018-58042 A , gas purification apparatus, machine translation, 2018.*

(Continued)

*Primary Examiner* — Jafar F Parsa
(74) *Attorney, Agent, or Firm* — WENDEROTH, LIND & PONACK, L.L.P.

(57) ABSTRACT

Provided are a method for producing a purified gas, which, when a valuable material is generated from a waste-derived raw material gas, can efficiently remove a phase transitioning impurity contained in the raw material gas, a method for producing a valuable material, a gas purification apparatus, and an apparatus for producing a valuable material. A method for producing a purified gas, comprising removing an impurity in a waste-derived raw material gas, the method comprising: a solid-phased impurity removing step S11 of passing the raw material gas through a phase transitioning impurity removing unit to remove a solid-phased phase (Continued)

transitioning impurity in the raw material gas; and an impurity removing step S12 of passing the raw material gas after the solid-phased impurity removing step through a pressure swing adsorption apparatus combined with a vacuum pump to remove an impurity in the raw material gas.

8 Claims, 12 Drawing Sheets

(58) Field of Classification Search
CPC ... C10K 1/04; C10K 1/32; C10K 1/02; C10K 1/06; C07C 29/1518; C10J 2300/1665
See application file for complete search history.

(56) References Cited

FOREIGN PATENT DOCUMENTS

| | | |
|---|---|---|
| CN | 109563421 | 4/2019 |
| JP | 6-83772 | 10/1994 |
| JP | 2007-45857 | 2/2007 |
| JP | 2008-222882 | 9/2008 |
| JP | 2014-50406 | 3/2014 |
| JP | 2016-187332 | 11/2016 |
| JP | 6097895 | 3/2017 |
| JP | 6134347 | 5/2017 |
| JP | 2018-58042 | 4/2018 |

OTHER PUBLICATIONS

JP 2016-187332 A, gas purification apparatus, machine translation, 2016.*
Office Action issued Oct. 26, 2024 in Chinese Patent Application No. 202080065349.7, with English-language Translation.
Zhang, Weiping (ed.). "Waste Gas Treatment in Building Materials Industry," National Environmental Protection Administration China Environmental Protection Agency Environmental Science Press, May 31, 1996, pp. 197-198.
International Search Report (ISR) issued Nov. 2, 2020 in International (PCT) Application No. PCT/JP2020/035837.

* cited by examiner

METHOD FOR PRODUCING PURIFIED GAS, METHOD FOR PRODUCING VALUABLE MATERIAL, GAS PURIFICATION DEVICE, AND DEVICE FOR PRODUCING VALUABLE MATERIAL

TECHNICAL FIELD

The present invention relates to a method for producing a purified gas, comprising removing an impurity contained in a raw material gas derived from a waste, a method for producing a valuable material, a gas purification apparatus, and an apparatus for producing a valuable material.

BACKGROUND ART

A technology for gasifying various wastes such as an industrial waste and a general waste by thermal decomposition is known (see, for example, PTL 1). According to this method, a raw material gas including large amounts of carbon monoxide and hydrogen can be obtained by thermally decomposing a waste. A waste-derived raw material gas can be used for various applications, and for example, it has been attempted to convert such a raw material gas into a valuable material such as ethanol by using a microbial catalyst, a metal catalyst, or the like (see, for example, PTL 2).

A waste-derived raw material gas includes a phase transitioning impurity that can phase transition between the gas phase and the solid phase, including a sublimating substance such as naphthalene, 1-naphthol, and 2-naphthol, when a substance including a large amount of a non-carbon component such as a municipal solid waste (MSW) is gasified. This type of phase transitioning impurity, even if it is initially gas phase when generated in a waste treatment facility, may be changed into solid-phase depending on the temperature conditions of the mainstream and the like and adhere to a filter installed in the mainstream and thereby cause the filter to be clogged. Because of this, the filter must be replaced frequently, which complicates maintenance and increases operating costs.

A waste-derived raw material gas includes a large amount of water, and when the raw material gas is cooled at once in order to remove the water and the phase transitioning impurity, the solid-phased phase transitioning impurity and a liquid-phased impurity such as soot and tar will be captured by the filter, causing the filter to be severely clogged. For this reason, in order to separately remove the water and the phase transitioning impurity in the raw material gas, a method involving carrying out a cooling step of the raw material gas in two stages has been proposed (see, for example, PTL 3).

CITATION LIST

Patent Literature

PTL 1: JP 2007-45857 A
PTL 2: JP 2014-050406 A
PTL 3: JP 6134347 B

SUMMARY OF INVENTION

Technical Problem

However, when the amount of the phase transitioning impurity included in the raw material gas is large, a removal treatment by an adsorption method may be insufficient even if the cooling step is carried out in two steps or the cooling temperature is lowered. In that case, the filter installed in the mainstream may be clogged, and the problems of complicated maintenance and increased operating costs remain. Further, in the cooling step, a large amount of energy is required to excessively lower the temperature, which causes the problem of increase in operating costs. In addition, excessively lowering the temperature in the cooling step may also cause an adverse effect such as freezing in the mainstream.

The present invention has been made in view of the above conventional problems, and an object thereof is to provide a method for producing a purified gas, which, when a valuable material is generated from a waste-derived raw material gas, can efficiently remove a phase transitioning impurity contained in the raw material gas, a method for producing a valuable material, a gas purification apparatus, and an apparatus for producing a valuable material.

Solution to Problem

As a result of diligent studies, the present inventor has found that the above problem can be solved by removing a phase transitioning impurity in the raw material gas by a pressure swing adsorption apparatus combined with a vacuum pump, and completed the present invention described below. That is, the present invention provides the following [1] to [18].

[1] A method for producing a purified gas, comprising removing an impurity in a waste-derived raw material gas, the method comprising: a solid-phased impurity removing step of passing the raw material gas through a phase transitioning impurity removing unit to remove a solid-phased phase transitioning impurity in the raw material gas; and an impurity removing step of passing the raw material gas after the solid-phased impurity removing step through a pressure swing adsorption apparatus combined with a vacuum pump to remove an impurity in the raw material gas.

[2] The method for producing a purified gas according to [1], wherein the method comprises a step of cooling the raw material gas in a preceding stage before the step of passing the raw material gas through the phase transitioning impurity removing unit.

[3] The method for producing a purified gas according to [2], wherein a cooling temperature in the cooling step is 20° C. or more.

[4] The method for producing a purified gas according to any one of [1] to [3], wherein the method further comprises a solid-liquid impurity removing step of passing an exhaust gas discharged from the vacuum pump through a solid-liquid impurity removing unit to remove a solid phase impurity and a liquid phase impurity in the raw material gas.

[5] The method for producing a purified gas according to any one of [1] to [4], wherein the solid-liquid impurity removing unit is a mist separator.

[6] The method for producing a purified gas according to any one of [1] to [5], wherein an exhaust gas discharged from the vacuum pump is allowed to flow through at least one of a plurality of discharge paths that can be selected.

[7] The method for producing a purified gas according to any one of [1] to [6], wherein a pressure of an exhaust gas discharged from the vacuum pump is measured by a pressure gage.

[8] The method for producing a purified gas according to any one of [2] to [7], wherein the cooling step cools the raw material gas to 10° C. or more and 30° C. or less, which is equal to or less than a phase transition temperature.

[9] A method for producing a valuable material, comprising contacting a purified gas obtained by the method for producing a purified gas according to any one of [1] to [8] with an organic catalyst to obtain a valuable material.

[10] A gas purification apparatus removing an impurity in a waste-derived raw material gas, the apparatus comprising: a phase transitioning impurity removing unit removing a solid-phased phase transitioning impurity in the raw material gas; and a pressure swing adsorption apparatus which is combined with a vacuum pump and removes an impurity in the raw material gas from which the solid-phased phase transitioning impurity has been removed in the phase transitioning impurity removing unit.

[11] The gas purification apparatus according to [10], wherein the apparatus further comprises a cooling unit cooling the raw material gas in a preceding stage before a step of passing the raw material gas through the phase transitioning impurity removing unit.

[12] The gas purification apparatus according to [11], wherein a cooling temperature by the cooling unit is 20° C. or more.

[13] The gas purification apparatus according to any one of [10] to [12], wherein the apparatus further comprises a solid-liquid impurity removing unit removing a solid phase impurity and a liquid phase impurity in an exhaust gas discharged from the vacuum pump.

[14] The gas purification apparatus according to any one of [10] to [13], wherein the solid-liquid impurity removing unit is a mist separator.

[15] The gas purification apparatus according to any one of [10] to [14], wherein the vacuum pump comprises a plurality of discharge paths that can each be selected as a flow path of the raw material gas to be discharged.

[16] The gas purification apparatus according to any one of [10] to [15], wherein the gas purification apparatus comprises a pressure gage measuring a pressure of the raw material gas to be discharged, on a discharge side of the vacuum pump.

[17] The gas purification apparatus according to any one of [11] to [16], wherein the cooling unit cools the raw material gas to 10° C. or more and 30° C. or less, which is equal to or less than a phase transition temperature.

[18] An apparatus for producing a valuable material, comprising: the gas purification apparatus according to any one of [10] to [17]; and a valuable material generation unit having an organic catalyst to be contacted with a purified gas obtained by the gas purification apparatus.

Advantageous Effects of Invention

According to the present invention, a method for producing a purified gas, which, when a valuable material is generated from a waste-derived raw material gas, can efficiently remove a phase transitioning impurity contained in the raw material gas, a method for producing a valuable material, a gas purification apparatus, and an apparatus for producing a valuable material can be provided.

DESCRIPTION OF EMBODIMENTS

Hereinafter, embodiments of the present invention will be described with reference to the drawings. In the descriptions of the drawings below, the same or similar parts are represented by the same or similar reference signs. However, the drawings are schematic, and the relationship between the thickness and the plane dimensions, the ratio of the thickness of each layer, and the like are different from the actual ones. Therefore, specific thickness and dimensions should be determined in light of the following descriptions. In addition, it goes without saying that parts having different dimensional relationships and ratios are included even between the drawings.

First Embodiment

Figure 1:
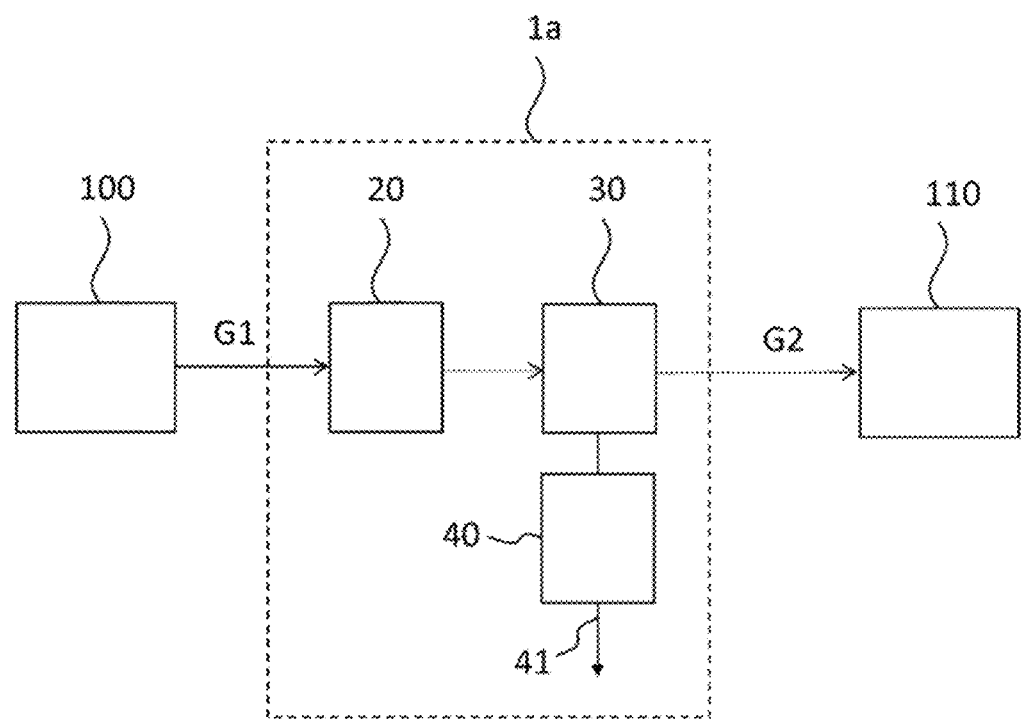
FIG. 1 is a schematic view illustrating a gas purification apparatus according to a first embodiment of the present invention.

As illustrated in FIG. 1, a gas purification apparatus 1a according to a first embodiment of the present invention is provided in connection with a raw material gas generation facility 100 and a valuable material generation reaction unit 110. The raw material gas generation facility 100 is a facility that generates a raw material gas G1, which is a waste-derived gas. The raw material gas G1 generated by the raw material gas generation facility 100 is introduced into the gas purification apparatus 1a. The gas purification apparatus 1a is a facility that removes an impurity contained in the raw material gas G1 introduced to generate a purified gas G2. The purified gas G2 generated by the gas purification apparatus 1a is introduced into the valuable material generation reaction unit 110. The valuable material generation reaction unit 110 is a facility that generates a valuable material such as ethanol from the purified gas G2 introduced.

In addition, as used herein, the "raw material gas" refers to a gas obtained by gasification at the raw material gas generation facility 100. In addition, the "purification" refers to removing an impurity included in a gas by purifying and separating the gas.

In addition, as used herein, the flow from the purification of the raw material gas G1 obtained by gasification at the raw material gas generation facility 100 to the entry into a fermenter of the valuable material generation reaction unit 110 is referred to as the mainstream. On the other hand, the flow other than the mainstream refers to a flow exhausted from a vacuum pump 40 or the like, which will be described later.

<Raw Material Gas Generation Facility>

The raw material gas generation facility 100 is a facility that gasifies a waste to purify a waste-derived raw material gas. For the gasification of the waste, for example, a gasification furnace may be used. The gasification furnace is a furnace that burns (incompletely burns) a carbon source, and examples thereof include a kiln gasification furnace, a fixed bed gasification furnace, a fluidized bed gasification furnace, a shaft type furnace, a plasma gasification furnace, and a carbonization furnace. The temperature at which a waste is gasified into a raw material gas is not particularly limited, and is usually 100 to 2,500° C., preferably 700 to 1,500° C., and more preferably 1,100 to 1,300° C.

The waste to be gasified may be an industrial waste such as an industrial solid waste or a general waste such as a municipal solid waste (MSW), and is not particularly limited as long as it is a combustible substance such as a plastic waste, garbage, a waste tire, and a biomass waste, a food waste, a building material, a wood, a wood chip, a fiber, and paper.

The raw material gas G1 obtained by gasifying a waste may be a synthetic gas including carbon monoxide and hydrogen, and may further include at least one of carbon dioxide, oxygen, and nitrogen. The raw material gas G1 includes water, and also includes an impurity such as a gas phase impurity such as hydrogen sulfide, hydrogen chloride, prussic acid, ammonia, NOx, SOx, acetylene, and BTEX (benzene, toluene, ethylbenzene, xylene), a solid or liquid phase impurity which is solid phase or liquid phase such as soot and tar, and a phase transitioning impurity. The phase transitioning impurity refers to an impure substance (excluding water) where when most thereof is gas phase when it is delivered from the raw material gas generation facility 100, but it can become solid phase with phase-transition in the process of being transported to the valuable material generation unit 110 and a part or the whole thereof, and examples thereof include a sublimating substance such as naphthalene, 1-naphthol, and 2-naphthol.

When the raw material gas G1 is a synthetic gas, it includes carbon monoxide and hydrogen. In addition, the raw material gas G1 preferably includes carbon monoxide in an amount of 0.1% by volume or more and 80% by volume or less, and hydrogen in an amount of 0.1% by volume or more and 80% by volume or less. In addition, the synthetic gas composing the raw material gas G1 may contain carbon dioxide. The raw material gas G1 preferably contains carbon dioxide in an amount of 0.1% by volume or more and 70% by volume or less.

In addition, the carbon monoxide concentration of the raw material gas G1 is preferably 10% by volume or more and 70% by volume or less, and more preferably 20% by volume or more and 50% by volume or less. In addition, the hydrogen concentration of the raw material gas G1 is preferably 10% by volume or more and 70% by volume or less, and more preferably 20% by volume or more and 50% by volume or less.

In addition, the carbon dioxide concentration of the raw material gas G1 is not particularly limited, and is preferably 0.1% by volume or more and 40% by volume or less, and more preferably 0.3% by volume or more and 30% by volume or less. The carbon dioxide concentration is particularly preferably lowered when ethanol is generated by an organic catalyst, and from such a viewpoint, the carbon dioxide concentration is more preferably 0.5% by volume or more and 25% by volume or less.

The nitrogen concentration of the raw material gas G1 is usually 40% by volume or less, and preferably 1% by volume or more and 20% by volume or less.

In addition, the oxygen concentration of the raw material gas G1 is usually 5% by volume or less, and preferably 1% by volume or less. In addition, the oxygen concentration is preferably as low as possible and may be 0% by volume or more. However, in general, oxygen is inevitably contained in many cases, and the oxygen concentration is practically 0.001% by volume or more.

The concentrations of carbon monoxide, carbon dioxide, hydrogen, nitrogen, and oxygen in the raw material gas G1 can be set to predetermined ranges by appropriately changing burning conditions such as the type of a waste, the gasification temperature in the raw material gas generation step, and the oxygen concentration of a supply gas at the time of gasification. Examples of methods therefor include a method involving using a waste having a high ratio of hydrocarbons (carbon and hydrogen) such as a waste plastic if the concentration of carbon monoxide or hydrogen is to be changed, and supplying a gas having a high oxygen concentration at the raw material gas generation facility 11 if the nitrogen concentration is to be reduced.

Further, the concentration of each component of carbon monoxide, carbon dioxide, hydrogen, and nitrogen may be appropriately adjusted in the raw material gas G1. The concentration may be adjusted by adding at least one of these components to the raw material gas G1.

The % by volume of each substance in the raw material gas in the raw material gas G1 described above means the % by volume of each substance in the raw material gas immediately before being introduced into the gas purification apparatus 1a described later, and when a preceding stage treatment described later is carried out, it is the % by volume of each substance after the preceding stage treatment.

<Gas Purification Apparatus>

The gas purification apparatus 1a includes a phase transitioning impurity removing unit 20 and a pressure swing adsorption apparatus 30 combined with a vacuum pump 40. The phase transitioning impurity removing unit 20 is provided in a subsequent stage after a cooling unit 10, and the pressure swing adsorption apparatus 30 is provided in a subsequent stage after the phase transitioning impurity removing unit 20.

As used herein, the "subsequent stage" means a subsequent stage along the supply flow of a raw material gas, and the "preceding stage" means a preceding stage along the supply flow of the raw material gas. The supply flow of the raw material gas G1 means the flow from the introduction of the raw material gas G1 into the gas purification apparatus 1a to the emission from the gas purification apparatus 1a as a purified gas G2, and in the present embodiment, it means the flow of the gas from the raw material gas generation facility 100 to the valuable material generation unit 110.

For the gas purification apparatus 1a, a preceding stage treatment unit, although not shown, is preferably provided in a preceding stage before the phase transitioning impurity removing unit 20, and the raw material gas G1 may be appropriately pretreated at the preceding stage treatment unit before being supplied to the gas purification apparatus 1a. The preceding stage treatment unit removes various impurities, water, carbon dioxide, and the like included in the raw material gas G1. Of course, the preceding stage treatment unit may be omitted.

<Preceding Stage Treatment Unit>

The preceding stage treatment unit is not particularly limited, and examples thereof include a scrubber and a desulfurization apparatus. The scrubber contacts a cleaning liquid consisting of water or an oil with the raw material gas, and removes at least a part of a water-soluble impurity and an oil-soluble impurity from the raw material gas G1. Examples of the water-soluble impurity include an acid gas such as hydrogen sulfide, hydrogen chloride, and prussic acid, a basic gas such as ammonia, and an oxide such as NOx and SOx. In addition, examples of the oil-soluble impurity include BTEX, naphthalene, 1-naphthol, and 2-naphthol.

<Phase Transitioning Impurity Removing Unit>

The phase transitioning impurity removing unit 20 captures and removes a solid-phased phase transitioning impurity in the raw material gas G1 introduced into the phase transitioning impurity removing unit 20.

The phase transitioning impurity removing unit 20 is not particularly limited as long as it can remove the solid-phased phase transitioning impurity, and a mist separator can also be adopted. The mist separator is not particularly limited, and examples thereof include a filter of a metal, a resin, a fiber, a ceramic, or the like, and a combination thereof may be used. The filter may have a single-layer mesh structure or a multi-layer mesh structure. The coarseness of the filter may be such that it can remove the solid-phased phase transitioning impurity, and by making the coarseness of the filter relatively coarse, clogging of the filter with the solid-phased phase transitioning impurity, condensed water, and the like can be suppressed and the frequency of filter replacement can be reduced.

As used herein, the "removing" means removing at least a part of a substance to be removed from a raw material gas to reduce the concentration of the substance to be removed in the gas, and is not limited to complete removal of the substance to be removed.

<Pressure Swing Adsorption Apparatus (PSA)>

The pressure swing adsorption apparatus 30 is combined with the vacuum pump 40, and removes an impurity in the raw material gas G1 from which the solid-phased phase transitioning impurity has been removed at the phase transitioning impurity removing unit 20.

The pressure swing adsorption apparatus 30 is not particularly limited as long as it can adsorb and remove a gas phase impurity such as carbon dioxide and BTEX, and examples thereof include a pressure vacuum swing adsorption (PVSA) apparatus into which a vacuum pump 40 is integrated.

The pressure swing adsorption apparatus 30 is an apparatus that has an adsorption tower filled with an adsorbent and repeats a purification step of adsorbing an impurity on the adsorbent with which the adsorption tower is filled by changing a pressure to remove the impurity and a regeneration step of desorbing the impurity adsorbed on the adsorbent. The adsorbent used in the pressure swing adsorption apparatus 30 may be composed of zeolite, silica gel, activated carbon, or the like, and zeolite or silica gel is preferable and zeolite is more preferable, from the viewpoint of efficiently removing a gas phase impurity such as carbon dioxide and BTEX.

The vacuum pump 40 decompresses an adsorption unit provided with the adsorbent of the pressure swing adsorption apparatus 30 to desorb the gas phase impurity adsorbed on the adsorbent and promote emission. The gas phase impurity desorbed by the vacuum pump 40 is discharged through a discharge path 41 provided in the vacuum pump 40. That is, the vacuum pump 40 can prevent the gas phase impurity from accumulating on the surface of the adsorbent of the pressure swing adsorption apparatus 30 and can maintain the adsorbing ability of the adsorbent for a long period of time.

In addition, the vacuum pump 40 can remove not only the gas phase impurity adsorbed on the adsorbent but also the phase transitioning impurity and water remaining in the adsorbent by decompressing the pressure swing adsorption apparatus 30 in the regeneration step. When the raw material gas G1 is passed through the same adsorption unit in the subsequent purification step, the phase transitioning impurity and water remaining in the adsorbent can be prevented from being contained in the raw material gas G1 by the vacuum pump 40 removing a part of the phase transitioning impurity and water remaining in the adsorbent in the regeneration step. That is, the vacuum pump 40 can prevent the phase transitioning impurity and water remaining in the adsorbent from being contained in the raw material gas G1 in the purification step and stably supply the purified gas G2.

Hereinafter, the pressure swing adsorption apparatus 30 will be described in more detail with reference to FIG. 2. In the following descriptions, an example in which the pressure swing adsorption apparatus 30 has two adsorption towers will be described. However, the number of adsorption towers in the pressure swing adsorption apparatus 30 is not limited to two, and may be three or more.

Figure 2:
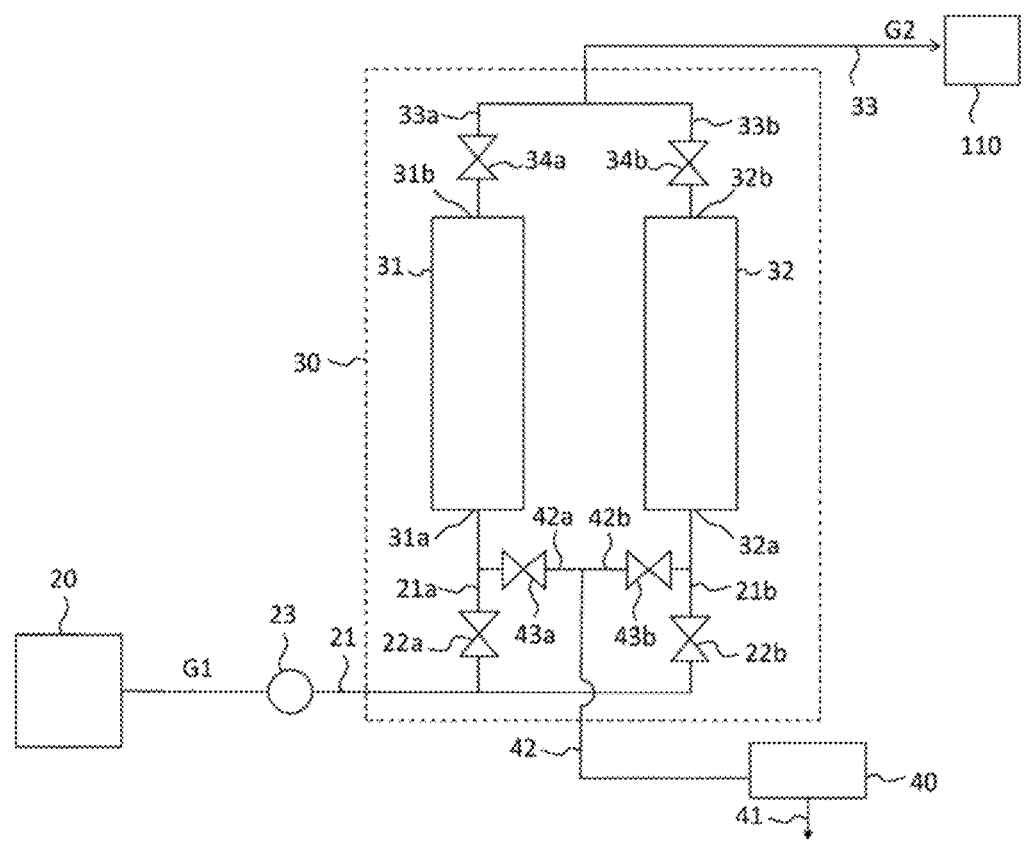
FIG. 2 is a schematic view illustrating a pressure swing adsorption apparatus provided in the gas purification apparatus according to the first embodiment of the present invention.

As illustrated in FIG. 2, the pressure swing adsorption apparatus 30 includes first and second adsorption towers 31 and 32, and an introduction path 21 for supplying the raw material gas G1 to the first and second adsorption towers 31 and 32 is connected.

The introduction path 21 is branched into two branch paths 21a and 21b, and the branch paths 21a and 21b are connected to one ends 31a and 32b of the first and second adsorption towers 31 and 32, respectively. Further, valves 22a and 22b are attached to the branch paths 21a and 21b, respectively.

In addition, a pressurizing device 23 is provided in the introduction path 21, and the raw material gas G1 pressurized by the pressurizing device 23 is supplied via the branch paths 21a and 21b to the first adsorption tower 31 or the second adsorption tower 32. The pressurizing device 23 may be any known one, and for example, a blower apparatus may be used. The raw material gas G1 may be pressurized to, for example, a gage pressure of 0 to 100 kPa, and preferably a gage pressure of 20 to 80 kPa by the pressurizing device 23.

In the introduction path 21, when the valve 22a is opened and the valve 22b is closed, the raw material gas G1 is supplied to the first adsorption tower 31. In addition, when the valve 22b is opened and the valve 22a is closed, the raw material gas G1 is supplied to the second adsorption tower 32.

By supplying the raw material gas G1 to the first adsorption tower 31 or the second adsorption tower 32, the purification step is carried out in each adsorption tower. Specifically, in one of the adsorption towers (either of the first and second adsorption towers 31 and 32) to which the raw material gas G1 is supplied, the raw material gas G1 is introduced into the inside of the tower from one end 31a or 32a thereof.

The raw material gas G1 introduced into the inside of the tower passes through the inside of the first adsorption tower 31 or the second adsorption tower 32 and is emitted from the other end 31b or 32b thereof. When the raw material gas G1 passes through the first adsorption tower 31 or the second adsorption tower 32, the impurity included in the raw material gas G1 is adsorbed by the adsorbent. Therefore, the gas emitted from the other end 31b or 32b of the first adsorption tower 31 or the second adsorption tower 32 is supplied as the gas purified by the adsorption tower 21 (purified gas G2) via a supply path 33 (33a or 33b) to a valuable material generation reaction unit 110.

The pressure swing adsorption apparatus 30 includes a vacuum pump 40, and the vacuum pump 40 is connected to the first adsorption tower 31 or the second adsorption tower 32 via a decompression path 42. The decompression path 42 is branched into two decompression paths 42a and 42b, and the decompression paths 42a and 42b are connected to one ends 31a and 32b of the first and second adsorption towers 31 and 32, respectively. The vacuum pump 40 can suck and decompress the inside of the first adsorption tower 31 or the second adsorption tower 32 to reduce the pressure via a decompression path 42a or a decompression path 42b. Valves 43a and 43b are provided in the decompression paths 42a and 42b, respectively.

In the first adsorption tower 31, by opening the valve 43a, closing the valve 34a, and carrying out the decompression by the vacuum pump 40 with the valve 43b closed, the regeneration step is carried out in the first adsorption tower 31. In addition, in the second adsorption tower 32 as well, by opening the valve 43b, closing the valve 34b, and carrying out the decompression by the vacuum pump 40 with the valve 43a closed, the regeneration step is carried out in the second adsorption tower 32.

In addition, the above regeneration step may be allowed to proceed in parallel with the purification step. Specifically, while passing the waste-derived raw material gas G1 through one of the adsorption towers, the other adsorption tower is sucked by the vacuum pump 40 to create a decompressed state, and then after the vacuuming is completed, purging with a purge gas such as nitrogen gas may be carried out to carry out the regeneration step in the other adsorption tower. The purge gas used in the regeneration step is introduced into the inside of the first and second adsorption towers 31 and 32 from purge paths (not shown) provided at the other ends 31b and 32b thereof, respectively. The purge gas introduced into the inside of the towers passes through the inside of the first and second adsorption towers 31 and 32 and is exhausted as an exhaust gas from one ends 31a and 32b of the first and second adsorption towers 31 and 32, respectively, via the decompression path 42.

Further, in each of the first and second adsorption towers 31 and 32, opening and closing of each valve may be repeated to alternately repeat the above purification step and regeneration step. In the present embodiment, a plurality of adsorption towers are provided as described above, and the raw material gas G1 is sequentially purified by the plurality of adsorption towers to continuously purify the raw material gas by the adsorption towers.

In the regeneration step, the vacuum pump 40 not only removes the gas phase impurity adsorbed on the adsorbent for regeneration, but also removes the phase transitioning impurity and water remaining in the adsorbent, by decompressing the first and second adsorption towers 31 and 32. The phase transitioning impurity and water remaining in the adsorbent removed by the vacuum pump 40 are discharged through a discharge path 41. When the raw material gas G1 is passed through the same adsorption unit in the subsequent purification step, the phase transitioning impurity and water remaining in the adsorbent can be prevented from being contained in the raw material gas G1 by the vacuum pump 40 removing a part of the phase transitioning impurity and water remaining in the adsorbent in the regeneration step. That is, the vacuum pump 40 can prevent the phase transitioning impurity and water remaining in the adsorbent from being contained in the raw material gas G1 in the purification step and stably supply the purified gas G2.

The purification step carried out in each of the adsorption towers 31 and 32 of the pressure swing adsorption apparatus 30 may be continuously carried out for a predetermined time, for example, 0.1 to 10 minutes and preferably 0.5 to 5 minutes.

In addition, each of the first and second adsorption towers 31 and 32 is decompressed by the vacuum pump 40 to, for example, a gage pressure of 0 to −101.3 kPa and preferably a gage pressure of −60 to −98 kPa in the regeneration step. By setting the pressure inside each adsorption tower within the above range, the impurity adsorbed on the adsorbent can be appropriately desorbed. Further, the decompression by the vacuum pump 40 in each adsorption tower may be carried out for about the same time as the that of the purification step or for a shorter time from the viewpoint of the power consumed by the vacuum pump, for example, for a shorter time by 0 to 70% and preferably 5 to 50% than the time of the purification step.

<Valuable Material Generation Reaction Unit>

The gas from which the impurity has been removed by the pressure swing adsorption apparatus 30 is appropriately treated by a subsequent stage treatment unit (not shown), if necessary, and then supplied to the valuable material generation unit 110 as the purified gas G2.

The subsequent stage treatment unit is not particularly limited, and examples thereof include a temperature swing adsorption apparatus, a metal catalyst such as copper and palladium, and various cleaning apparatuses such as various filters. Of course, the subsequent stage treatment unit may be omitted.

The valuable material generation unit 110 has a catalyst such as an organic catalyst or a metal catalyst. In the valuable material generation unit 110, the purified gas G2 comes into contact with a catalyst such as an organic catalyst or a metal catalyst and is converted into a valuable material. The valuable material is not particularly limited as long as it is an organic compound that can be converted from a synthetic gas, and ethanol is preferable. Ethanol can be easily synthesized from hydrogen and carbon monoxide included in a synthetic gas. In addition, as the catalyst used in the valuable material generation unit 110, an organic catalyst is preferable. As the organic catalyst, a gas-utilizing microorganism is preferably used.

In the case of conversion to ethanol using a gas-utilizing microorganism, a synthetic gas is supplied to the inside of a fermenter filled with the gas-utilizing microorganism, and the synthetic gas is microbially fermented in the microbial fermenter to produce ethanol. As the gas-utilizing microorganism, for example, anaerobic bacteria disclosed in PTL 2 mentioned above, WO 2011/087380 A, US 2013/0065282 A, and the like can be used.

Although not shown, a purification unit including a distillation tower is provided in the subsequent stage of the valuable material generation reaction unit 110, and the purification unit extracts a valuable material such as ethanol.

[Method for Producing Purified Gas]

Figure 3:
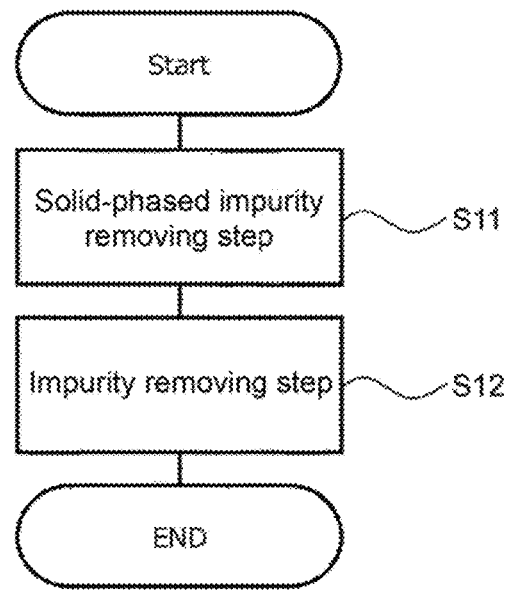
FIG. 3 is a flowchart illustrating a method for producing a purified gas according to the first embodiment of the present invention.

As illustrated in FIG. 3, the method for producing a purified gas according to the first embodiment includes a solid-phased impurity removing step S11 and an impurity removing step S12. Hereinafter, the method for producing a purified gas according to the first embodiment will be described with reference to FIG. 1 and FIG. 3.

<Solid-Phased Impurity Removing Step>

In the solid-phased impurity removing step S11, a solid-phased phase transitioning impurity in the raw material gas G1 is removed.

Specifically, by passing the raw material gas G1 through a filter provided in the phase transitioning impurity removing unit 20, the solid-phased phase transitioning impurity is removed by the filter.

In addition, the filter provided in the phase transitioning impurity removing unit 20 can remove a part of a solid-liquid phase impurity such as soot and tar in the raw material gas G1.

<Impurity Removing Step>

In the impurity removing step S12, the raw material gas G1 after the solid-phased impurity removing step S11 is passed through the pressure swing adsorption apparatus 30 combined with the vacuum pump 40 to remove an impurity in the raw material gas G1.

Specifically, by passing the raw material gas G1 after the solid-phased impurity removing step S11 through an adsorption unit provided with the adsorbent of the pressure swing adsorption apparatus 30, a gas phase impurity such as carbon dioxide and BTEX in the raw material gas G1 is adsorbed by the adsorption unit and removed.

Subsequently, the vacuum pump 40 decompresses the adsorption unit provided with the adsorbent of the pressure swing adsorption apparatus 30 to desorb the gas phase impurity adsorbed on the adsorbent. Then, the vacuum pump 40 discharges an exhaust gas including the gas phase impurity through the discharge path 41.

In addition, the vacuum pump 40 can remove not only the gas phase impurity adsorbed on the adsorbent but also the phase transitioning impurity and water remaining in the adsorbent by decompressing the pressure swing adsorption apparatus 30. Then, the vacuum pump 40 discharges an exhaust gas including the phase transitioning impurity and water through the discharge path 41.

The purified gas G2 generated through the impurity removing step S12 is introduced into the valuable material generation reaction unit 110, and the valuable material generation reaction unit 110 generates a valuable material such as ethanol from the purified gas G2.

According to the gas purification apparatus and the method for producing a purified gas according to the first embodiment of the present invention, by using a pressure swing adsorption apparatus combined with a vacuum pump, the vacuum pump can prevent an impurity from accumulating on the surface of an adsorbent of the pressure swing adsorption apparatus and can maintain the adsorbing ability of the adsorbent of the pressure swing adsorption apparatus for a long period of time.

In addition, the vacuum pump can emit a part of the phase transitioning impurity in the raw material gas and thus, together with the phase transitioning impurity removing unit, can remove the phase transitioning impurity contained in the raw material gas, and clogging of the filter installed in the mainstream with the phase transitioning impurity can be suppressed. Because of this, maintenance such as filter replacement can be alleviated, and operating costs can be reduced.

In addition, the vacuum pump can emit a part of the water in the raw material gas and thus can play a part of the role of emitting the water in the raw material gas, and operating costs such as the amount of electricity used can be reduced as compared with emitting the water in the raw material gas only by cooling and condensing the raw material gas using the cooling unit.

In addition, according to the gas purification apparatus and the method for producing a purified gas according to the first embodiment of the present invention, an impurity in a raw material gas, which is a waste-derived gas, can be efficiently removed, and a gas-utilizing microorganism can be stably cultured.

Second Embodiment

Next, a second embodiment of the present invention will be described. In the following, the descriptions of the second embodiment that overlap with those of the first embodiment will be omitted, and the differences from the first embodiment will be described.

Figure 4:
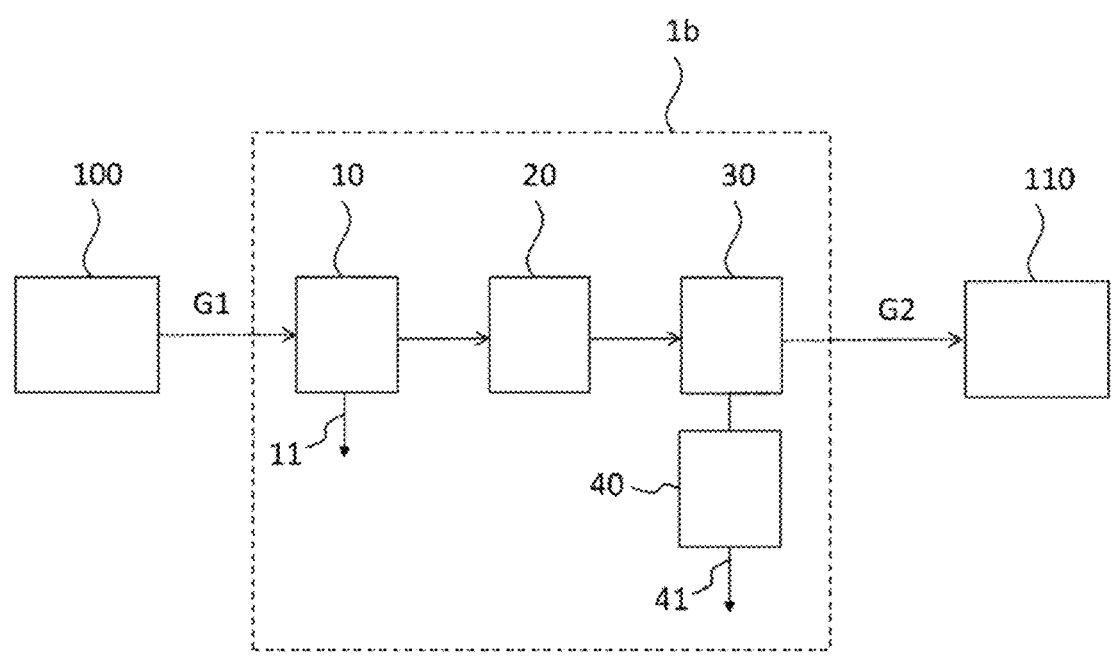
FIG. 4 is a schematic view illustrating a gas purification apparatus according to a second embodiment of the present invention.

As illustrated in FIG. 4, a gas purification apparatus 1b in the second embodiment further includes a cooling unit 10 on the upstream side of a phase transitioning impurity removing unit 20.

<Cooling Unit>

The cooling unit 10 cools the raw material gas G1 introduced therein so that a phase transitioning impurity is changed into solid-phase. The cooling temperature is determined according to the amount of the phase transitioning impurity removed by the cooling unit 10. The temperature of the raw material gas G1 at the time of generation at a raw material gas generation facility 100 or at the time of delivery from the raw material gas generation facility 100 is higher than normal temperature, for example, about 30° C. to several hundred degrees C. Here, the phase transition temperature refers to the temperature at which a phase transitioning impurity phase-transitions, and specifically refers to the temperature at which a phase transitioning impurity sublimates. That is, the cooling target temperature of the cooling unit 10 is set within a range in which a phase transition of the phase transitioning impurity contained in the raw material gas G1 (for example, sublimation and solidification of naphthalene) can sufficiently occur. The cooling target temperature of the cooling unit 10 may encompass the phase transition temperature of the phase transitioning impurity, and is preferably 5° C. or more and 40° C. or less, more preferably 10° C. or more and 40° C. or less, further preferably 15° C. or more and 35° C. or less, and more further preferably 20° C. or more and 30° C. or less. When the cooling temperature of the cooling unit 10 is equal to or more than the above lower limit, it is possible to prevent clogging due to freezing of a tube, a filter, and the like in the mainstream. In addition, when the cooling temperature is equal to or more than the above lower limit, the energy for lowering the temperature can be suppressed and operating costs can be reduced. When the configuration of the present invention is adopted, no problem occurs because the pressure swing adsorption apparatus 30 can remove the phase transitioning impurity even if the cooling unit 10 is operated under a relatively high temperature condition of, for example, 20° C. or more; and the energy required for operation of the vacuum pump 40 is smaller than the energy required for cooling, and thus this case is energetically advantageous. Further, when the cooling temperature is equal to or more than the above lower limit, it is also possible to prevent the phase transitioning impurity from being too solid-phased and causing clogging in the filter or the like.

The temperature of the raw material gas G1 between the cooling unit 10 and the pressure swing adsorption apparatus 30 is equal to or more than the above lower limit, and thus a component of the raw material gas G1 does not freeze to cause clogging in the filter or the like. In addition, by appropriately adjusting the temperature, it is also possible to prevent the phase transitioning impurity in the raw material gas G1 from being too solid-phased and causing clogging in the filter or the like.

Examples of the cooling unit 10 include a heat exchanger (chiller) and a scrubber.

The heat exchanger (chiller) as the cooling unit 10 is preferably a shell and tube type heat exchanger composed of a plurality of cooling tubes. When the cooling unit 10 is a shell and tube type heat exchanger, the cooling tubes are preferably straight tubes from the viewpoint of ease of cleaning, and the cooling tubes are preferably arranged in parallel with each other with the tube axes facing up and down. A refrigerant such as ethylene glycol flows outside the cooling tubes, and cools the raw material gas G1 introduced into the cooling unit 10 flowing inside the cooling tubes. The cooling unit 10 includes a drain path 11, and emits the phase transitioning impurity and water in the raw material gas G1 condensed by cooling from the drain path 11.

The scrubber as the cooling unit 10 is preferably a water scrubber. When the cooling unit 10 is a water scrubber, it includes a circulating water supply path (not shown) for supplying circulating water inside the water scrubber. In addition, the water scrubber preferably has a filler inside for increasing the gas-liquid contact efficiency between the raw material gas G1 and the circulating water. Further, the water scrubber has a heat exchanger outside, and the circulating water inside the water scrubber is kept at a constant temperature by cooling the heat exchanger. The raw material gas G1 introduced into the cooling unit 10 comes into gas-liquid contact with the circulating water inside the water scrubber and is cooled. The cooling unit 10 includes a drain path 11, and emits the phase transitioning impurity and water in the raw material gas G1 condensed by cooling together with the circulating water from the drain path 11.

Figure 5:
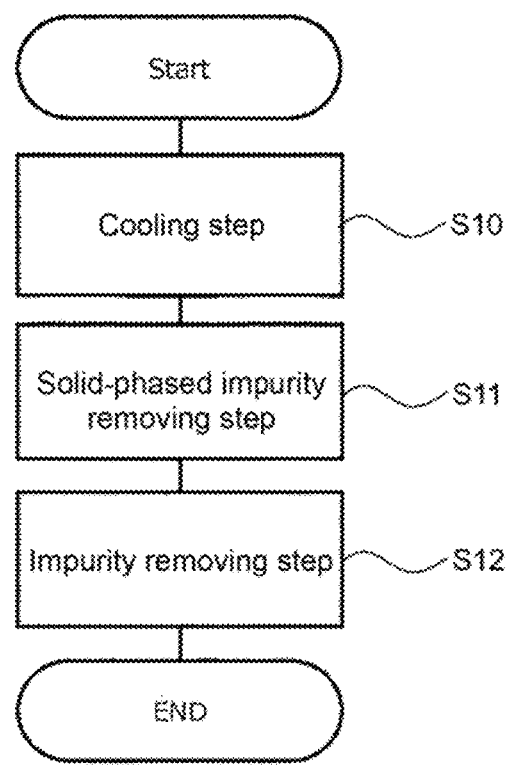
FIG. 5 is a flowchart illustrating a method for producing a purified gas according to the second embodiment of the present invention.

As illustrated in FIG. 5, the method for producing a purified gas according to the second embodiment further includes a cooling step S10.

<Cooling Step>

In the cooling step S10, the raw material gas G1 is cooled to the phase transition temperature of the phase transitioning impurity.

Specifically, the raw material gas G1 generated by the raw material gas generation facility 11 is cooled by the cooling unit 10. The raw material gas G1 generated by the raw material gas generation facility 100 is cooled to a temperature equal to or less than the phase transition temperature of the phase transitioning impurity by the cooling unit 10 to change the phase transitioning impurity contained in the raw material gas G1 into solid-phase.

In addition, by cooling the raw material gas G1 by the cooling unit 10, a part of the water in the raw material gas G1 is condensed, and the resulting condensed water is emitted from the drain path 11.

According to the gas purification apparatus and the method for producing a purified gas according to the second embodiment of the present invention, the same effects as described in the gas purification apparatus and the method for producing a purified gas according to the first embodiment can be exhibited.

Further, according to the gas purification apparatus and the method for producing a purified gas according to the second embodiment of the present invention, a raw material gas can be cooled to the transition temperature or less by a cooling unit to change a phase transitioning impurity contained in the raw material gas into solid-phase, and the phase transitioning impurity can be efficiently removed by a phase transitioning impurity removing unit. Because of this, a filter installed in the mainstream can be prevented from being clogged with the phase transitioning impurity, and maintenance such as filter replacement can be alleviated and operating costs can be reduced.

Third Embodiment

Next, a third embodiment of the present invention will be described. In the following, the descriptions of the third embodiment that overlap with those of the second embodiment will be omitted, and the differences from the second embodiment will be described.

Figure 6:
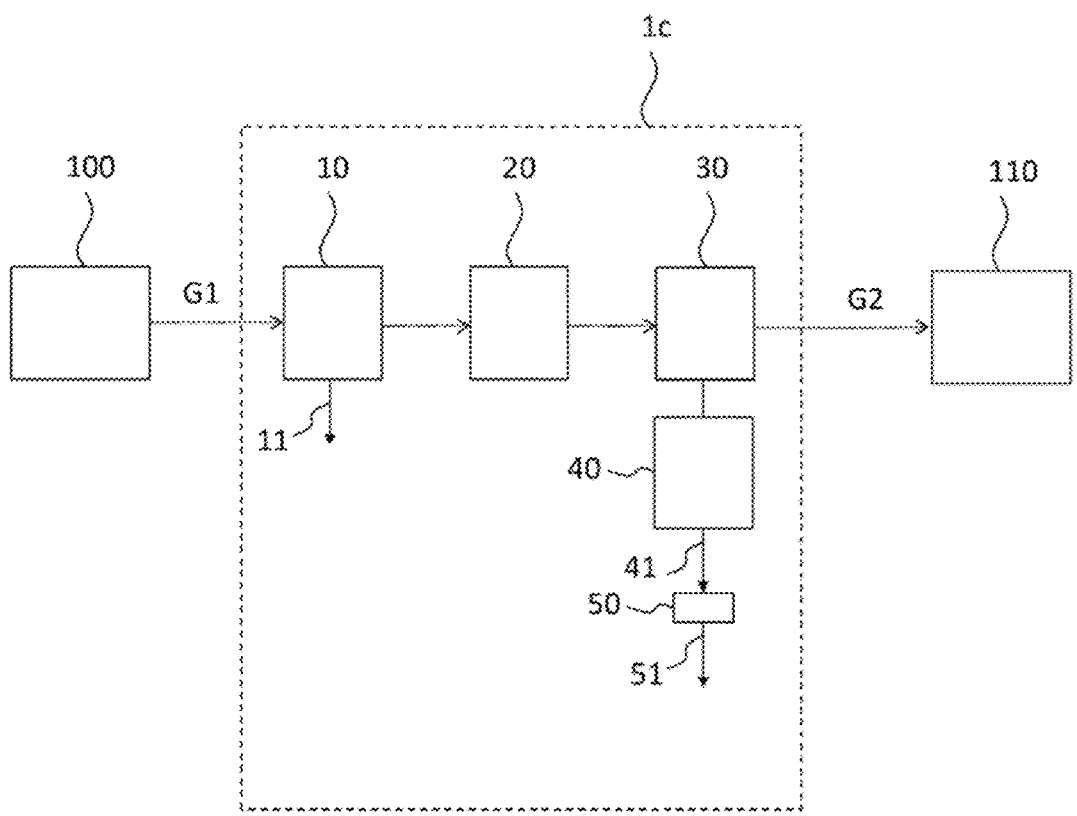
FIG. 6 is a schematic view illustrating a gas purification apparatus according to a third embodiment of the present invention.

As illustrated in FIG. 6, a gas purification apparatus 1c in the third embodiment further includes a solid-liquid impurity removing unit 50 in a discharge path 41 on the downstream side of a vacuum pump 40.

The solid-liquid impurity removing unit 50 removes a solid phase impurity and a liquid phase impurity in an exhaust gas discharged from the vacuum pump 40. Specifically, the solid-liquid impurity removing unit 50 removes an impurity that is gas phase after being discharged from the vacuum pump 40 but is solid-phased or liquid-phased when the impurity is separated from the vacuum pump 40 and thereby put under normal temperature and normal pressure. Therefore, the solid-liquid impurity removing unit 50 is preferably provided in the discharge path 41 on the downstream side of the vacuum pump 40, after a place where an impurity to be solid-phased or liquid-phased occurs. Examples of the solid phase impurity removed by the solid-liquid impurity removing unit 50 include a phase transitioning impurity and dust solid-phased by a decrease in temperature. Examples of the liquid phase impurity removed by the solid-liquid impurity removing unit 50 include a liquid-phased water droplet.

The solid-liquid impurity removing unit 50 is not particularly limited as long as it can remove a solid phase impurity and a liquid phase impurity, and examples thereof include a mist separator. The mist separator is not particularly limited, and examples thereof include a filter of a metal, a resin, a fiber, a ceramic, or the like, and a combination thereof may be used. The filter may have a single-layer mesh structure or a multi-layer mesh structure. The coarseness of the filter may be such that it can remove a solid phase impurity and a liquid phase impurity, and by making the coarseness of the filter relatively coarse, clogging of the filter with a solid phase impurity, a liquid phase impurity, condensed water, and the like can be suppressed and the frequency of filter replacement can be reduced.

Figure 7:
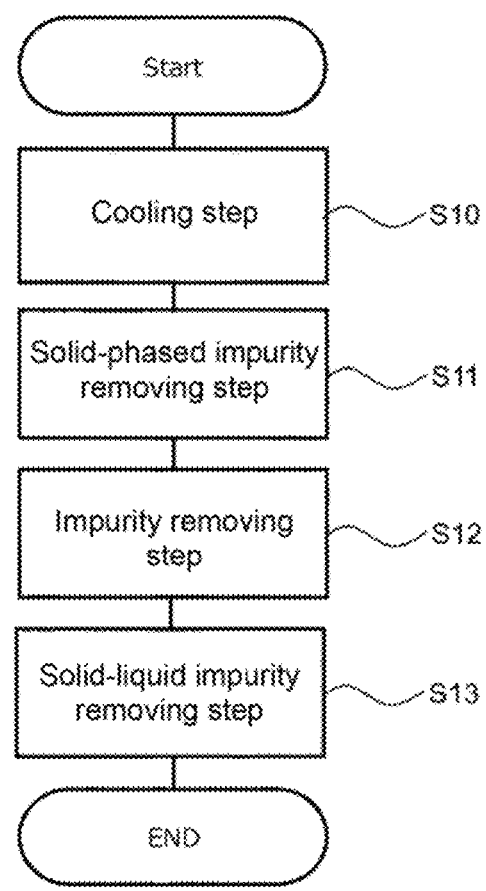
FIG. 7 is a flowchart illustrating a method for producing a purified gas according to the third embodiment of the present invention.

As illustrated in FIG. 7, the method for producing a purified gas according to the third embodiment further includes a solid-liquid impurity removing step S13.

<Solid-Liquid Impurity Removing Step>

In the solid-liquid impurity removing step S13, as shown in FIG. 6, an exhaust gas discharged from the vacuum pump 40 is passed through the solid-liquid impurity removing unit 50 to remove the solid phase impurity and the liquid phase impurity in the exhaust gas.

Specifically, by passing the raw material gas G1 after the impurity removing step S12 through the solid-liquid impurity removing unit 50, an impurity in the raw material gas G1 that has not been able to be completely removed in the solid-phased impurity removing step S11 and the impurity removing step S12 is removed. In particular, clogging in the discharge paths 41 and 51 after the discharge from the vacuum pump 40 can be suppressed by the solid-liquid impurity removing unit 50 removing an impurity that is gas phase after being discharged from the vacuum pump 40, but is solid-phased or liquid-phased when the impurity is separated from the vacuum pump 40 and thereby put under normal temperature and normal pressure.

According to the gas purification apparatus and the method for producing a purified gas according to the third embodiment of the present invention, the same effects as described in the gas purification apparatuses and the methods for producing a purified gas according to the first and second embodiments can be exhibited.

Further, according to the gas purification apparatus and the method for producing a purified gas according to the third embodiment of the present invention, clogging in a discharge path of a vacuum pump can also be suppressed by a solid-liquid impurity removing unit removing a solid phase impurity and a liquid phase impurity in a raw material gas.

Fourth Embodiment

Next, a fourth embodiment of the present invention will be described. In the following, the descriptions of the fourth embodiment that overlap with those of the second embodiment will be omitted, and the differences from the second embodiment will be described.

Figure 8:
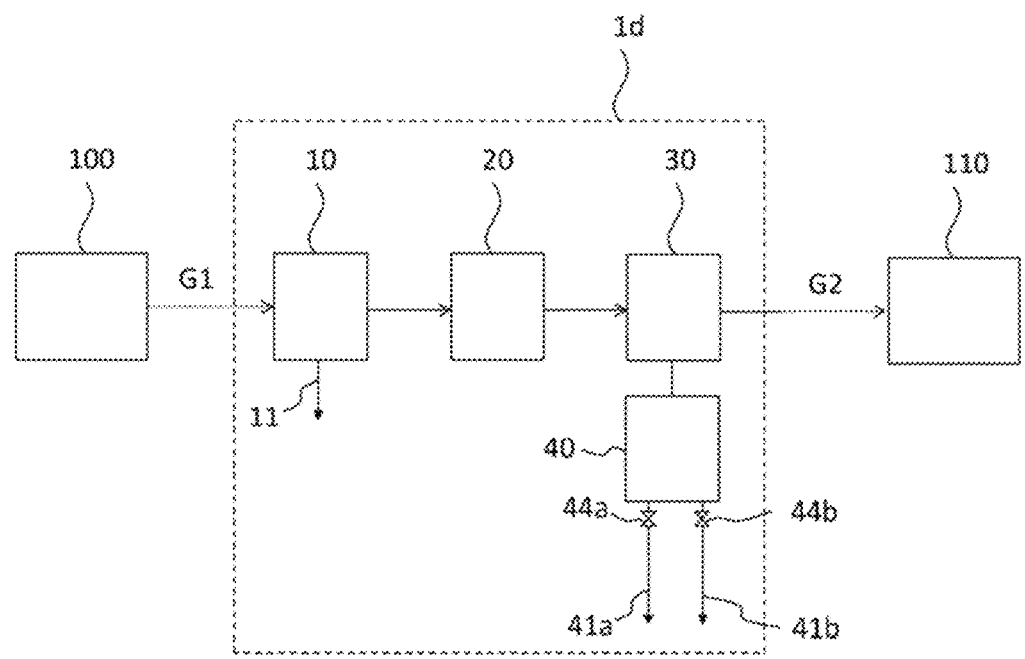
FIG. 8 is a schematic view (No. 1) illustrating a gas purification apparatus according to a fourth embodiment of the present invention.
Figure 9:
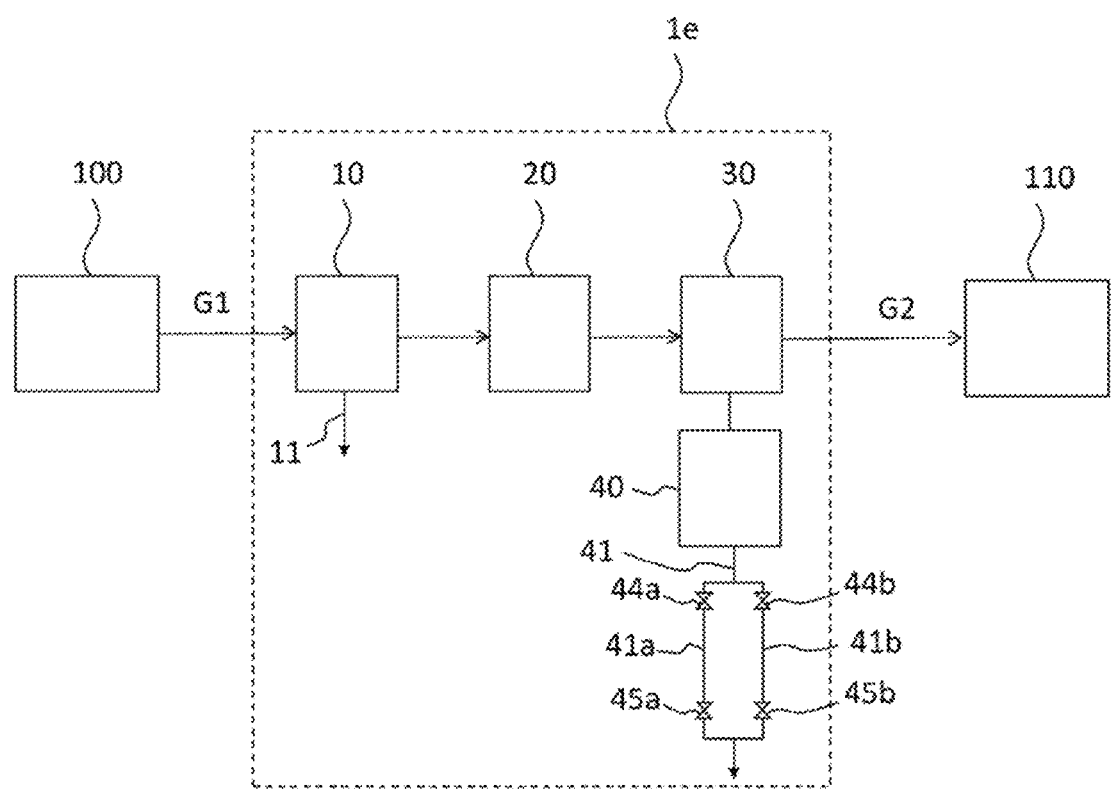
FIG. 9 is a schematic view (No. 2) illustrating a gas purification apparatus according to the fourth embodiment of the present invention.

As illustrated in FIG. 8 and FIG. 9, a vacuum pump 40 of each of gas purification apparatuses 1d and 1e according to the fourth embodiment includes a plurality of discharge paths 41a and 41b that can each be selected as a flow path of an exhaust gas to be discharged.

In the gas purification apparatus 1d illustrated in FIG. 8, the vacuum pump 40 includes the same number of discharge ports as that of the plurality of discharge paths 41a and 41b. In this case, the flow path of the exhaust gas to be discharged from the vacuum pump 40 can be selected by valves 44a and 44b provided in the discharge paths 41a and 41b, respectively. In the vacuum pump 40 in the gas purification apparatus 1d, when the valve 44a is opened and the valve 44b is closed, the exhaust gas is discharged through the discharge path 41a. In addition, in the vacuum pump 40 in the gas purification apparatus 1d, when the valve 44b is opened and the valve 44a is closed, the exhaust gas is discharged through the discharge path 41b.

In the gas purification apparatus 1e illustrated in FIG. 9, the vacuum pump 40 includes one discharge port and includes a plurality of discharge paths 41a and 41b branching from the discharge path 41 connected to the discharge port. In this case, the flow path of the exhaust gas to be discharged from the vacuum pump 40 can be selected by valves 44a and 44b on the upstream side and valves 45a and 45b on the downstream side provided in the discharge paths 41a and 41b, respectively. In the vacuum pump 40 in the gas purification apparatus 1e, when the valves 44a and 45a are opened and the valves 44b and 45b are closed, the exhaust gas is discharged through the discharge path 41a. In addition, in the vacuum pump 40 in the gas purification apparatus 1e, when the valves 44b and 45b are opened and the valves 44a and 45b are closed, the exhaust gas is discharged through the discharge path 41b.

According to the gas purification apparatus and the method for producing a purified gas according to the fourth embodiment of the present invention, the same effects as described in the gas purification apparatuses and the methods for producing a purified gas according to the first and second embodiments can be exhibited.

Further, according to the gas purification apparatus and the method for producing a purified gas according to the fourth embodiment of the present invention, by providing a plurality of discharge paths that can each be selected as a flow path of an exhaust gas to be discharged from a vacuum pump, even if any of the discharge paths is clogged, the operation can be continued by another discharge path. In addition, by providing a plurality of discharge paths that can each be selected as a flow path of an exhaust gas to be discharged from a vacuum pump, a discharge path that is not used for operation can be cleaned, and clogging can be prevented. Further, there are a plurality of discharge ports, and thus for example, even if one discharge port is clogged, the mainstream of the raw material gas is not blocked, and thus there are the following advantages: gas purification can be continuously carried out and the risk of stopping the supply of the raw material gas to a fermenter can be reduced or eliminated. Because of this, the purified raw material gas continuously enters the fermenter, which makes it possible to maintain the productivity of an organic substance and the activity of a catalyst. If the catalyst is a microorganism, the activity may decrease because of a sudden change in the raw material composition, or the microorganism may die at worst when the supply of the raw material gas is stopped.

On the other hand, conventionally, a tube of the cooling unit is clogged, and thus the mainstream of the raw material gas is blocked. In this case, the only way to prevent the mainstream from being blocked is to provide a plurality of cooling units, which requires a large cost and causes a problem such as the trouble of stream switching.

In addition, by increasing the diameter of the tube, the thermal conductivity to the outside air is lowered and the tube is unlikely to be cooled, and thus the amount of precipitation can be reduced. The larger the outer shape of the tube, the greater the cooling suppression effect; for example, the outer diameter of the tube is desirably 165.2 mm or more.

Fifth Embodiment

Next, a fifth embodiment of the present invention will be described. In the following, the descriptions of the fifth embodiment that overlap with those of the second embodiment will be omitted, and the differences from the second embodiment will be described.

Figure 10:
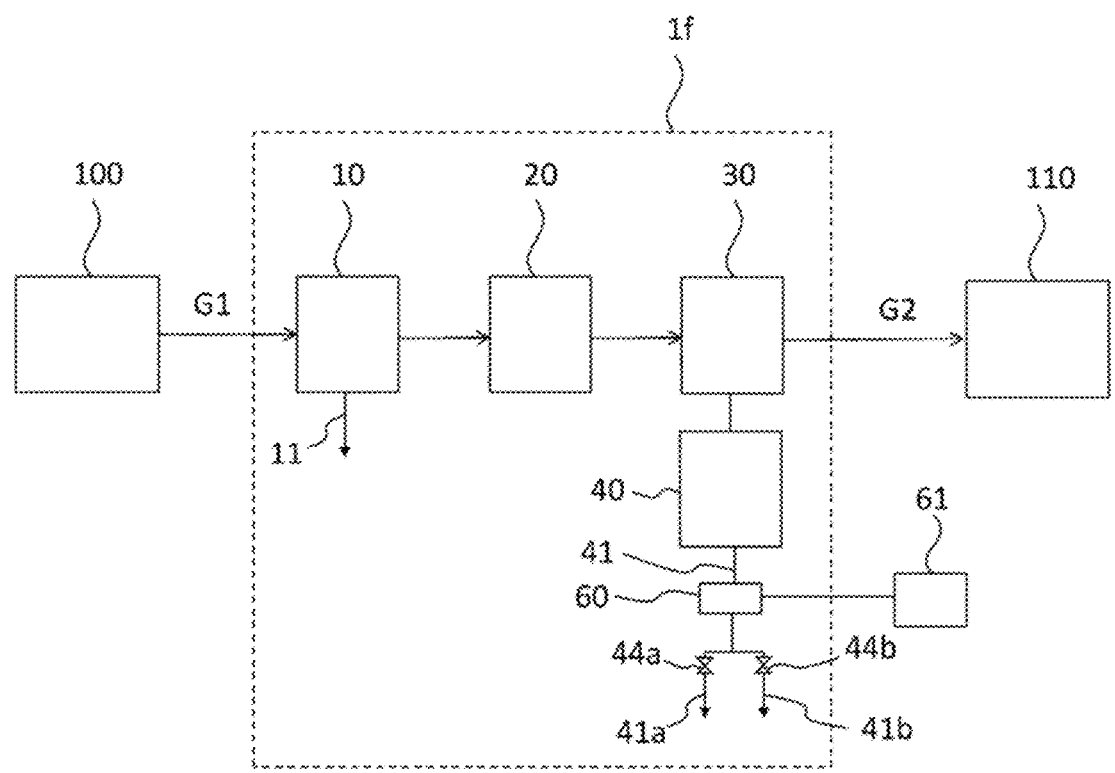
FIG. 10 is a schematic view illustrating a gas purification apparatus according to a fifth embodiment of the present invention.

As illustrated in FIG. 10, a gas purification apparatus 1f according to the fifth embodiment includes a pressure gage 60 measuring the pressure of an exhaust gas to be discharged on the discharge side of a vacuum pump 40.

The pressure gage 60 measures the pressure of the exhaust gas flowing on the discharge side (for example, through a discharge path 41) of the vacuum pump 40. The pressure gage 60 transmits measured pressure data to a control unit 61. The control unit 61 controls selection of a flow path of the exhaust gas to be discharged from the vacuum pump 40 based on the pressure data received. The control by the control unit 61 is, for example, a control in which when the pressure data received is higher than a predetermined value, it is determined that the currently selected flow path is clogged and another flow path is selected.

As illustrated in FIG. 10, the place at which the pressure gage 60 is installed is not limited to the discharge path 41 immediately after the discharge side of the vacuum pump 40, and the pressure gage 60 may be installed in a plurality of discharge paths 41*a* and 41*b*.

According to the gas purification apparatus and the method for producing a purified gas according to the fifth embodiment of the present invention, the same effects as described in the gas purification apparatuses and the methods for producing a purified gas according to the first and second embodiments can be exhibited.

Further, according to the gas purification apparatus and the method for producing a purified gas according to the fifth embodiment of the present invention, by providing a pressure gage measuring the pressure of an exhaust gas on the discharge side of a vacuum pump, the pressure in a discharge path can be known, and an abnormality such as pressure rise due to clogging of a discharge path or the like can be immediately detected and dealt with.

Other Embodiments

As described above, the present invention has been specifically described with reference to embodiments of the present invention, but the present invention is not limited to the above embodiments. In addition, various improvements can be made as long as these do not deviate from the gist of the present invention.

Figure 11:
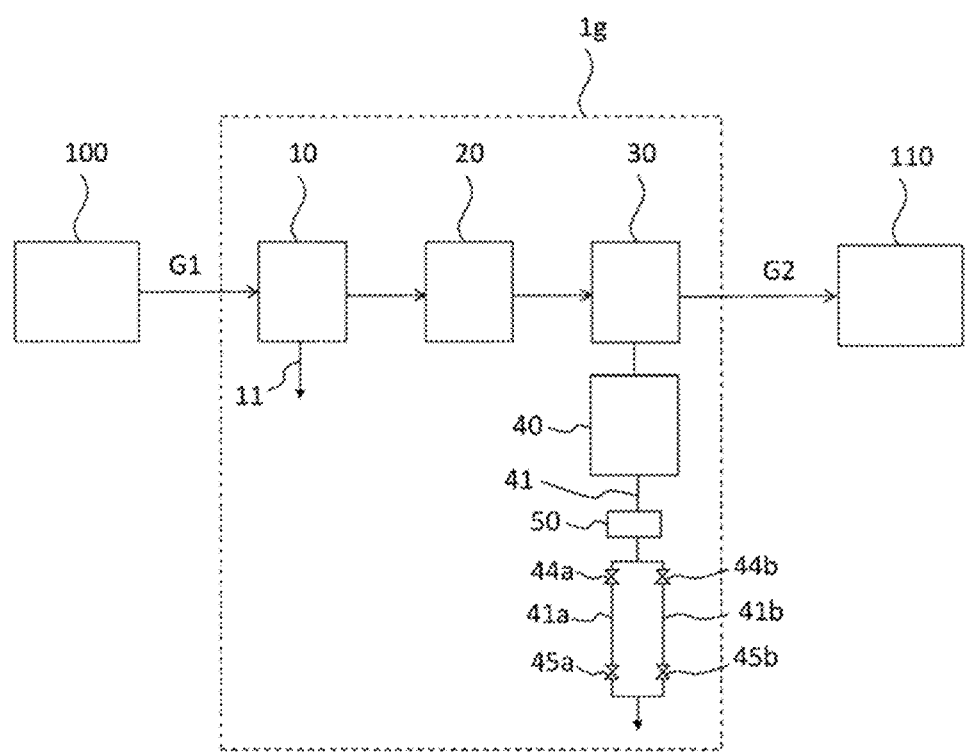
FIG. 11 is a schematic view (No. 1) illustrating a gas purification apparatus according to another embodiment of the present invention.
Figure 12:
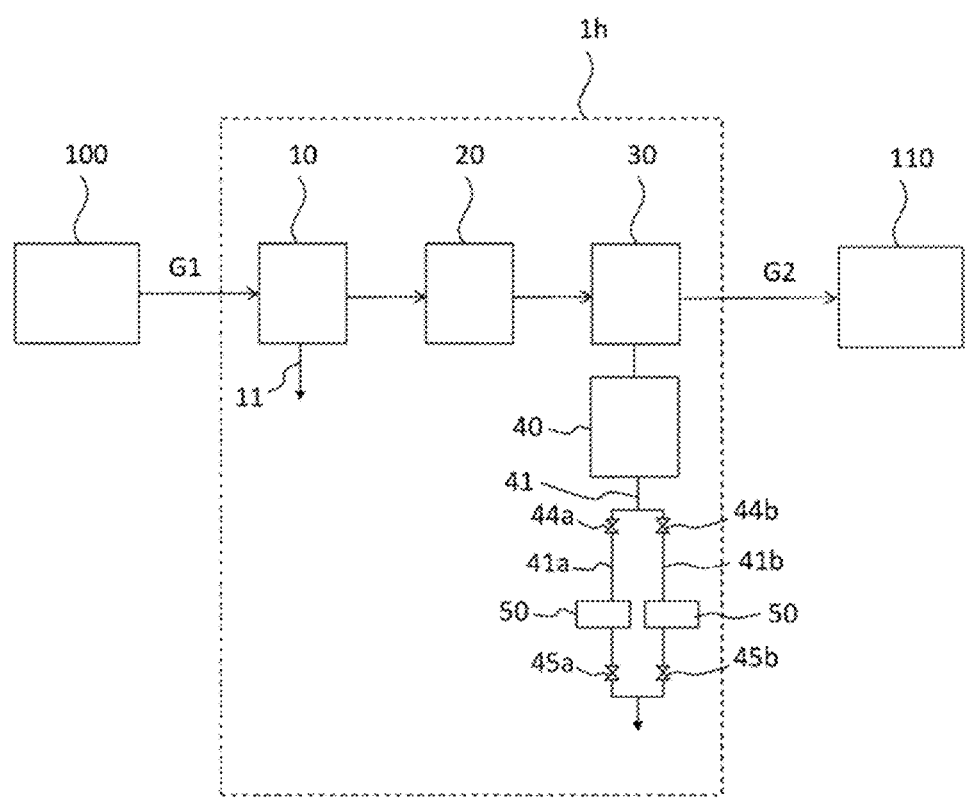
FIG. 12 is a schematic view (No. 2) illustrating a gas purification apparatus according to another embodiment of the present invention.
Figure 13:
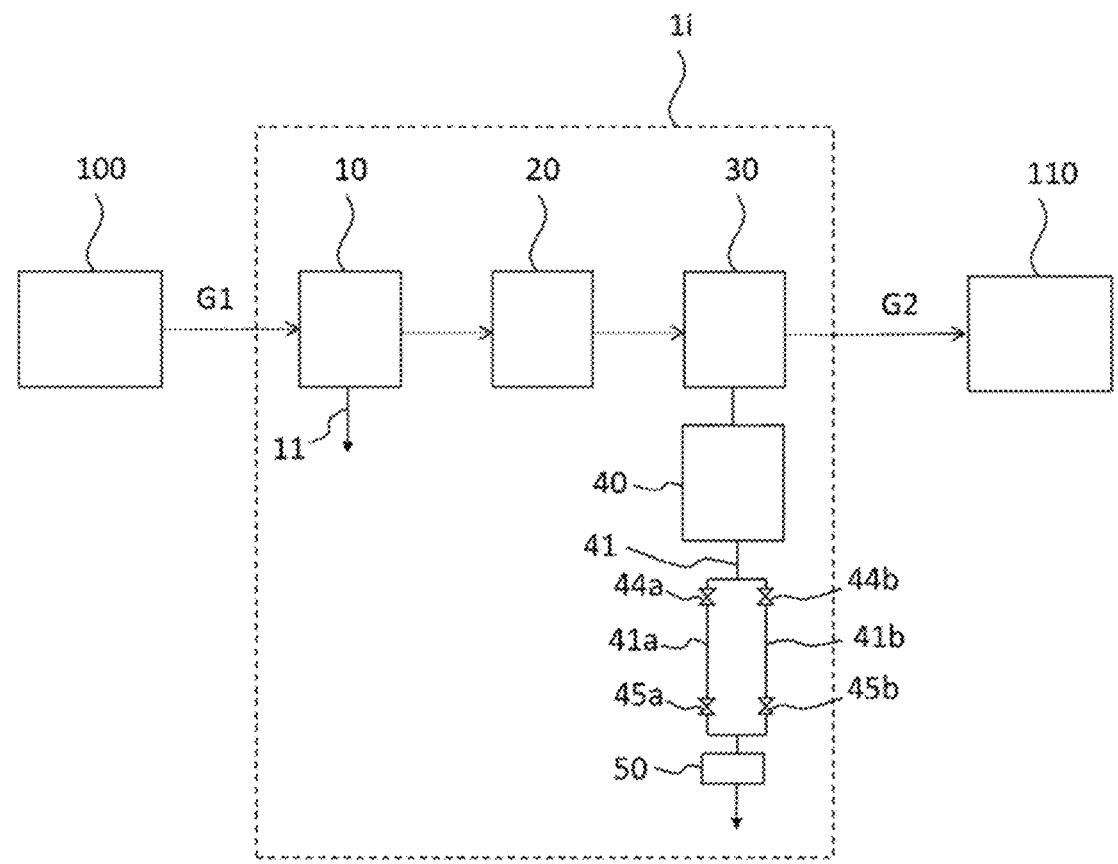
FIG. 13 is a schematic view (No. 3) illustrating a gas purification apparatus according to another embodiment of the present invention.

For example, the gas purification apparatus 1*c* according to the third embodiment and the gas purification apparatus 1*e* according to the fourth embodiment may be combined. Specifically, as a gas purification apparatus 1*g* according to another embodiment, as illustrated in FIG. 11, a solid-liquid impurity removing unit 50 may be provided immediately after the downstream side of a vacuum pump 40, before branching into a plurality of discharge paths 41*a* and 41*b*. In addition, as a gas purification apparatus 1*h* according to another embodiment, as illustrated in FIG. 12, a solid-liquid impurity removing unit 50 may be provided in each of a plurality of discharge paths 41*a* and 41*b*. In addition, as a gas purification apparatus 1*i* according to another embodiment, as illustrated in FIG. 13, a solid-liquid impurity removing unit 50 may be provided after a plurality of discharge paths 41*a* and 41*b* have merged.

REFERENCE SIGNS LIST

1*a* to 1*i*: Gas purification apparatuses
10: Cooling unit
11: Drain path
20: Phase transitioning impurity removing unit
21: Introduction path
22*a*, 22*b*: Valves
23: Pressurizing device
30: Pressure swing adsorption apparatus
31: First adsorption tower
32: Second adsorption tower
33, 33*a*, 33*b*: Supply paths
34*a*, 34*b*: Valves
40: Vacuum pump
41, 41*a*, 41*b*: Discharge paths
42, 42*a*, 42*b*: Decompression paths
43*a*, 43*b*: Valves
44*a*, 44*b*, 45*a*, 45*b*: Valves
50: Solid-liquid impurity removing unit
60: Pressure gage
61: Control unit
100: Raw material gas generation facility
110: Valuable material generation reaction unit

The invention claimed is:

1. A gas purification apparatus removing an impurity in a waste-derived raw material gas, the apparatus comprising:
a phase transitioning impurity removing unit removing a solid-phased phase transitioning impurity in the raw material gas;
a pressure swing adsorption apparatus which is combined with a vacuum pump and removes an impurity in the raw material gas from which the solid-phased phase transitioning impurity has been removed in the phase transitioning impurity removing unit; and
a pressure gage measuring a pressure of the raw material gas to be discharged, on a discharge side of the vacuum pump.

2. The gas purification apparatus according to claim 1, wherein the apparatus further comprises a cooling unit cooling the raw material gas in a preceding stage before a step of passing the raw material gas through the phase transitioning impurity removing unit.

3. The gas purification apparatus according to claim 2, wherein a cooling temperature by the cooling unit is 20° C. or more.

4. The gas purification apparatus according to claim 1, wherein the apparatus further comprises a solid-liquid impurity removing unit removing a solid phase impurity and a liquid phase impurity in an exhaust gas discharged from the vacuum pump.

5. The gas purification apparatus according to claim 1, wherein the solid-liquid impurity removing unit is a mist separator.

6. The gas purification apparatus according to claim 1, wherein the vacuum pump comprises a plurality of discharge paths that can each be selected as a flow path of the raw material gas to be discharged.

7. The gas purification apparatus according to claim 2, wherein the cooling unit cools the raw material gas to 5° C. or more and 40° C. or less, which is equal to or less than a phase transition temperature.

8. An apparatus for producing a valuable material, comprising: the gas purification apparatus according to claim 1; and a valuable material generating unit having an organic catalyst to be contacted with a purified gas obtained by the gas purification apparatus.

* * * * *